(12) United States Patent
Shah et al.

(10) Patent No.: US 12,310,727 B2
(45) Date of Patent: May 27, 2025

(54) ANALYTE SENSOR

(71) Applicants: PERCUSENSE, Valencia, CA (US); Rajiv Shah, Rancho Palos Verdes, CA (US); Katherine Wolfe, Dunwoody, GA (US); Bradley Liang, Bloomfield Hills, MI (US); Shaun Pendo, Wofford Heights, CA (US)

(72) Inventors: Rajiv Shah, Rancho Palos Verdes, CA (US); Katherine Wolfe, Dunwoody, GA (US); Bradley Liang, Bloomfield Hills, MI (US); Shaun Pendo, Wofford Heights, CA (US)

(*) Notice: Subject to any disclaimer, the term of this patent is extended or adjusted under 35 U.S.C. 154(b) by 0 days.

(21) Appl. No.: 18/499,746

(22) Filed: Nov. 1, 2023

(65) Prior Publication Data
US 2024/0057906 A1    Feb. 22, 2024

Related U.S. Application Data

(63) Continuation of application No. 17/260,678, filed as application No. PCT/US2019/042247 on Jul. 17, 2019, now abandoned.

(60) Provisional application No. 62/699,477, filed on Jul. 17, 2018.

(51) Int. Cl.
A61B 5/1473    (2006.01)
A61B 5/00      (2006.01)
A61B 5/145     (2006.01)

(52) U.S. Cl.
CPC .......... *A61B 5/1473* (2013.01); *A61B 5/6848* (2013.01); *A61B 5/14532* (2013.01); *A61B 5/14542* (2013.01); *A61B 5/14546* (2013.01); *A61B 2562/164* (2013.01)

(58) Field of Classification Search
CPC ........ A61B 2562/164; A61B 2562/166; A61B 2562/187; A61B 5/14503; A61B 5/14532; A61B 5/14546; A61B 5/1473; A61B 5/14865; A61B 5/6848; A61B 5/14542
See application file for complete search history.

(56) References Cited

U.S. PATENT DOCUMENTS

| | | | |
|---|---|---|---|
| 2011/0021889 A1 | 1/2011 | Hoss et al. | |
| 2013/0245412 A1* | 9/2013 | Rong | A61B 5/14532 600/347 |
| 2016/0338733 A1* | 11/2016 | Shah | A61B 5/14532 |
| 2017/0325725 A1* | 11/2017 | Shah | A61B 5/14532 |
| 2017/0328857 A1 | 11/2017 | Shah et al. | |
| 2018/0199873 A1* | 7/2018 | Wang | A61B 5/14546 |

(Continued)

FOREIGN PATENT DOCUMENTS

ES     2899901 T3    3/2022
WO     2018237259 A1  12/2018

OTHER PUBLICATIONS

International Search Report in Corresponding PCT Application No. PCT/US2019/042247 mailed Sep. 18, 2019. 4 pages.

*Primary Examiner* — Eric J Messersmith
(74) *Attorney, Agent, or Firm* — Leason Ellis LLP

(57) ABSTRACT

A sensor assembly is disclosed. The sensor assembly includes a piercing member with an interior and exterior. Also included within the sensor assembly is a sensor that is formed on a flexible substrate. The sensor includes a proximal end and a distal end where the distal end includes a flex that is terminated at a terminal end. The terminal end of the sensor being located within the interior of the piercing member.

20 Claims, 6 Drawing Sheets

(56) References Cited

U.S. PATENT DOCUMENTS

2018/0279926 A1  10/2018  Wolfe et al.
2019/0265186 A1  8/2019  Shah et al.

* cited by examiner

ANALYTE SENSOR

RELATED APPLICATIONS

This application is a continuation of U.S. application Ser. No. 17/260,678 filed Jan. 15, 2017, which is a U.S. National Stage Application under 35 U.S.C. § 371 of International Patent Application No. PCT/US2019/042247 filed Jul. 17, 2019, which claims the benefit of U.S. provisional application No. 62/699,477 filed Jul. 17, 2018, both of which are hereby incorporated by reference in their entireties for all purposes. The International Application was published on Jan. 23, 2020, as International Publication No. WO 2020/018696 A1.

FIELD OF THE INVENTION

The present invention is generally directed to insertion of devices that perform in vivo monitoring of at least one physiological parameter such as, but not limited to, perfusion, temperature or concentration of at least one analyte. In particular, minimally invasive insertion or placement of electrochemical sensors that provide real-time information regarding the presence or concentration of an analyte or analytes like glucose, oxygen or lactate within a subject.

BACKGROUND OF THE INVENTION

Diabetes is a growing healthcare crisis, affecting nearly 30 million people in the United States. Approximately 10 percent of those affected require intensive glucose and insulin management. In hospital patients, hypoglycemia in both diabetic and non-diabetic patients is associated with increased cost and short- and long-term mortality.

To prevent complications, diabetes requires ongoing management. Continuous glucose monitoring (CGM) has been shown in studies to be the most effective way to improve glucose control, whether used with insulin injections or a continuous insulin pump. CGM systems typically rely on sensors that implanted under the skin for time periods varying between days and weeks. Consistently inserting the sensor through the skin to a desired depth has proven challenging and various insertion techniques have lead to the development and implementation of various insertion tools. An additional development in diabetes therapy includes the artificial pancreas. The artificial pancreas couples CGM technology with an infusion pump that typically dispenses glucose. Commonly, artificial pancreas systems utilize two subdermal insertions; a first insertion for the CGM sensor and a second insertion for the glucose infusate location. Enabling a combined sensor and infusion set could potentially half the number of insertions for someone using an artificial pancreas.

Accordingly, it would be highly advantageous to simplify the insertion process to reduce the burden of CGM and artificial pancreas therapy. Simplification of insertion can mean many different things such as, but not limited to, improving repeatability of insertion depth and securely implanting sensors for the desired wear period. The claimed invention seeks to address many issues associated with inserting a sensor into the subdermal space.

BRIEF SUMMARY OF THE INVENTION

In one embodiment, a sensor assembly is disclosed. The sensor assembly includes a piercing member with an interior and exterior. Also included within the sensor assembly is a sensor that is formed on a flexible substrate. The sensor includes a proximal end and a distal end where the distal end includes a flex that is terminated at a terminal end. The terminal end of the sensor being located within the interior of the piercing member.

In another embodiment, a method of inserting a sensor into subdermal space is disclosed. The method includes and operation to couple a sensor to a piercing member. The distal end of the sensor including a flex that terminates in a terminal end. The flex enables placement of the terminal end of the sensor within a piercing bevel of the piercing member. In a subsequent operation the piercing member is inserted to a depth within the subdermal space, the sensor coupled to the piercing member being inserted to substantially the same depth as the piercing member. With another operation, the piercing member is retracted, the retraction of the piercing member decoupling the terminal end from within piercing bevel of the piercing member.

Other features and advantages of the invention will become apparent from the following detailed description, taken in conjunction with the accompanying drawings that illustrate, by way of example, various features of embodiments of the invention.

BRIEF DESCRIPTION OF THE DRAWINGS

FIG. 2C is a pseudo-isometric illustration of a sensor without the piercing member, in accordance with embodiments of the invention.

FIGS. 3A and 3B are exemplary front views of a portion of the sensor assembly, specifically, FIG. 3A includes the piercing member and the sensor while FIG. 3B is an illustration of the sensor without the piercing member, in accordance with embodiments of the present invention.

FIG. 4A illustrates the piercing member while FIG. 4B illustrates the sensor without the piercing member, in accordance with embodiments of the present invention.

DETAILED DESCRIPTION

Insertion of sensors or infusion cannulas into subdermal space can involve balancing a multitude of variables such as, but not limited to piercing member design or configuration (e.g., fully closed needle, sharp or partially closed needle/sharp), gauge of piercing member, insertion depth, reliability of insertion and likelihood of pullout. Many of the variables require consideration from the perspective of the user because the use of large needles or sharps or deeper insertion depths may be viewed as potentially uncomfortable or even painful. However, while substantial insertion depth may be viewed as uncomfortable, shallow insertion depth may be viewed as unreliable because motive forces imparted by the subject can result in the sensor being unintentionally pulled out.

Presented below are embodiments that are intended to reliably and securely insert a sensor within a subject at a relatively shallow insertion depth while maximizing surface area of the sensor being placed in subdermal space. Though various features of different embodiments may be discussed individually, the various features and embodiments should be viewed as potentially being combined within another embodiment or other embodiments so long the intended operation of the combined embodiments is not compromised. Accordingly, the features described in each embodiment should be viewed as being combinable with the other features and embodiments discussed within the following pages.

In many examples discussed below sensor structures are discussed in reference to glucose sensors. While embodiments and examples may be related to a specific analyte or even a particular plurality of analytes, the scope of the disclosure and claims should not be construed to be limited to the analytes and parameters specifically associated with diabetes. Rather it should be recognized that additional or other analytes and or parameters can be monitored to assist in the detection and diagnosis of various metabolic conditions or general physiological health.

Figure 1:
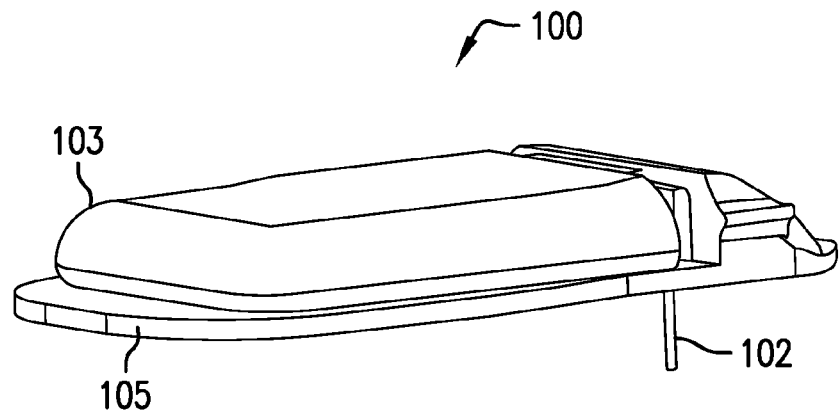
FIG. 1 is an exemplary pseudo-isometric illustration of a sensor assembly, in accordance with embodiments of the invention.

FIG. 1 is an exemplary pseudo-isometric illustration of a sensor assembly 100, in accordance with embodiments of the invention. The sensor assembly 100 may include components such as a piercing member 102 that is used to insert a sensor (not shown) in subdermal tissue or space. A base 105 is another component of the sensor assembly 100. The base 105 can include adhesive that removably couples the base 105 to a subject for a desired period of time. The base 105 also provides a mechanical structure to support the sensor and an insertion tool. The base 105 further provides a mechanical structure to support an electronic module 103 that can be pre-attached before, or installed after or during the insertion process. The electronics module 103 can include a computer processor, memory, computer instructions, bi-directional radios, a potentiostat and a power supply to enable the sensor to operate for a desired duration. In many embodiments the operational duration of a sensor is measured in days, or weeks.

In many embodiments, the sensor assembly 100 is similar to the embodiments described in U.S. patent application Ser. No. 15/816,549 filed on Nov. 17, 2017, which is herein incorporated by reference for all purposes. Some embodiments the sensor assembly 100 may require the use of a separate insertion tool while a separate insertion tool may be optional for other embodiments. In some embodiments, a portion of the sensor may be fixed to an interior feature of the base 105 prior to insertion while in other embodiments, the sensor may be incorporated within a separate insertion tool that removably couples a portion of the insertion tool with the base 105. Likewise, in many embodiments, the piercing member 102 may be integrated into the base 105 or as part of a separate insertion tool.

Figure 2A:
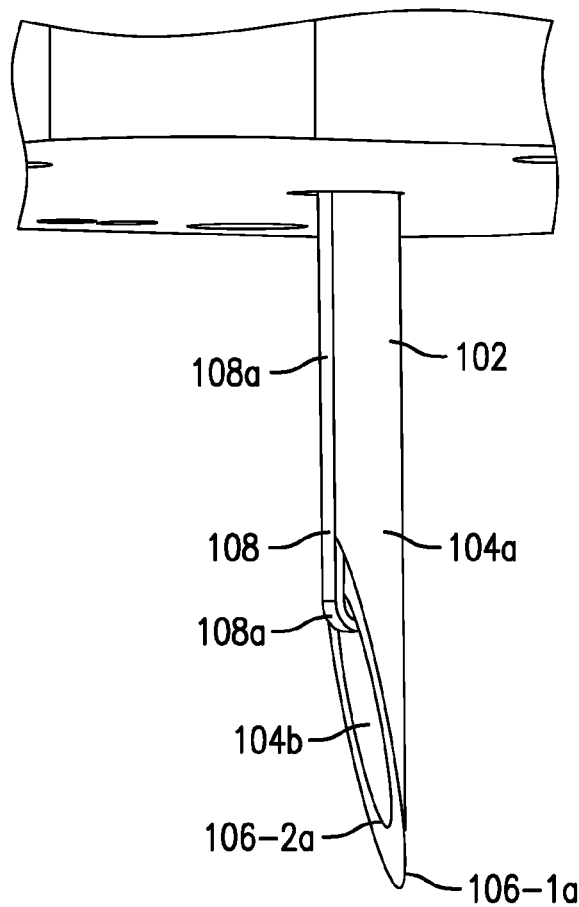
FIG. 2A is an exemplary pseudo-isometric illustration and FIG. 2B is a cross-section view of a sensor partially nested within a piercing member, in accordance with embodiments of the sensor assembly.
Figure 2B:
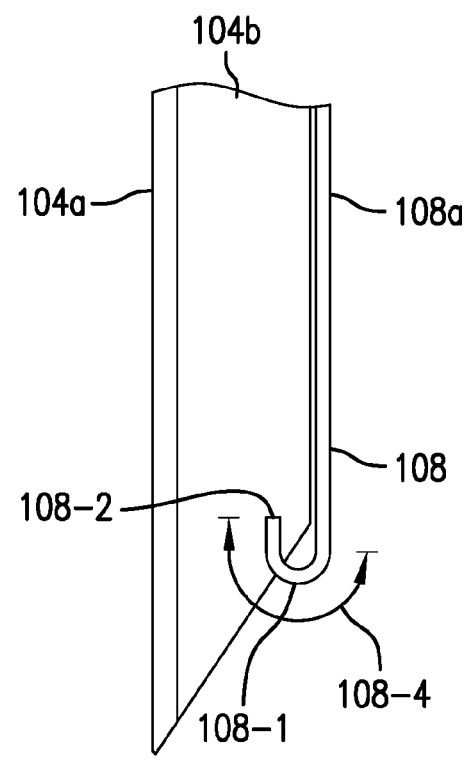

FIG. 2A is an exemplary pseudo-isometric illustration and FIG. 2B is a cross-section view of a sensor 108 partially nested within a piercing member 102, in accordance with embodiments of the sensor assembly 100. The piercing member 102 has an exterior 104a and an interior 104b. The piercing member 102 further includes an exterior piercing tip 106-1a and an interior piercing tip 106-2a. In many embodiments the piercing member 102 is a hollow needle having a beveled tip. The exterior piercing tip 106-1a being used to pierce the skin of a subject intending to use the sensor assembly. The beveled tip of the piercing member 102 in the figures is intended to be exemplary, in other embodiments different bevels, such as, but not limited to standard bevels, short bevels, true bevels, and the like can be used with sensors have a flex 108-1.

The sensor 108 has an a-side 108a and a b-side 108b. In many embodiments the b-side 108b of the sensor 108 is located adjacent to the exterior 104a of the piercing member 102. The sensor 108 further includes a distal end 108-4 that incorporates a flex 108-1. The flex 108-1 of the distal end 108-4 places the terminal end 108-2 within the interior 104b of the piercing member 102. In some embodiments the sensor 108 is configured to measure a single analyte. In other preferred embodiments, the sensor 108 is configured to measure a plurality of analytes. Exemplary analytes the sensor 108 can be configured to measure include, but are not limited to glucose, lactate, ketones, oxygen and the like.

Figure 2C:
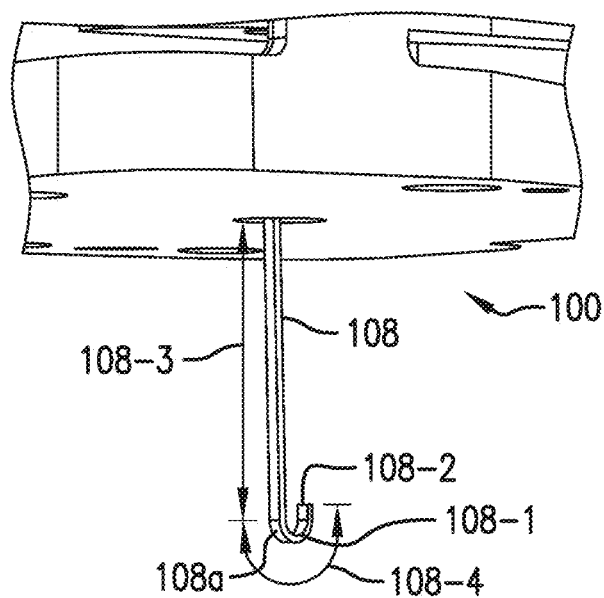
FIG. 2C is an exemplary pseudo-isometric illustration of the sensor without the piercing member seen in FIG. 2A.

FIG. 2C is an exemplary pseudo-isometric illustration of the sensor 108 without the piercing member 102 seen in FIG. 2A. This view illustrates sensor straight 108-3 that is substantially parallel with the piercing member 102 and extends to the flex 108-1 of the distal end 108-4. The flex 108-1, is intended to be defined broadly as at least some portion of the distal end 108-4 of the sensor 108 that is flexed, bent, folded or otherwise deformed at an angle. The flex 108-1 enables the terminal end 108-2 to be placed within a portion of a bevel of piercing member 102 while the sensor straight 108-3 is positioned along or adjacent the exterior 104a of the piercing member 102.

Figure 3A:
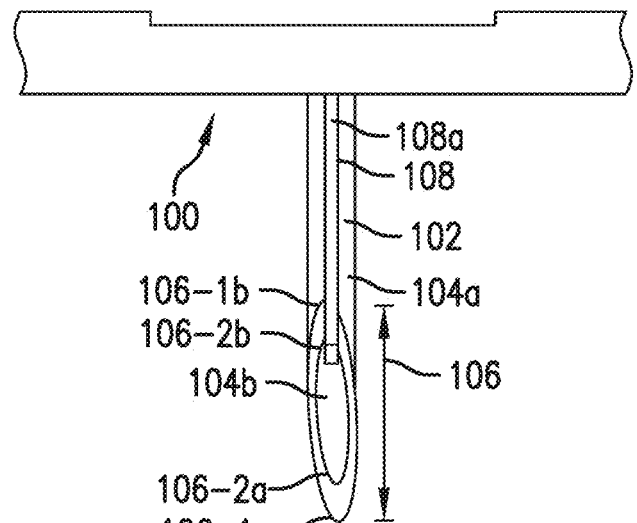
Figure 3B:
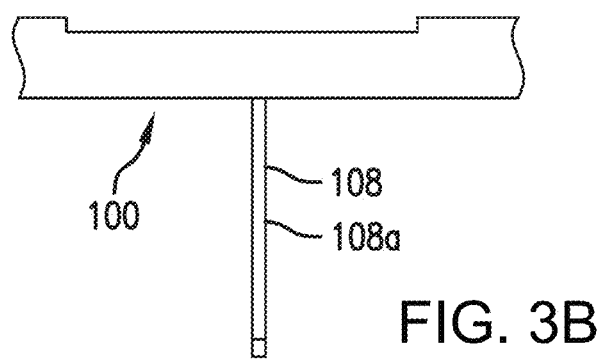

FIGS. 3A and 3B are exemplary front views of a portion of the sensor assembly 100, specifically, FIG. 3A includes the piercing member 102 and the sensor 108 while FIG. 3B is an illustration of the sensor 108 without the piercing member 102, in accordance with embodiments of the present invention. The piercing member 102 includes a piercing bevel 106. The piercing bevel 106 results in the piercing member 102 having a tip defined by exterior piercing tip 106-1a and interior piercing tip 106-2a. An upper portion of the piercing bevel 106 includes exterior trailing bevel 106-1b and interior trailing bevel 106-2b. The piercing bevel 106 further exposes interior 104 of the piercing member 102. Viewing FIG. 3A in conjunction with FIGS. 2A-2C illustrates how positioning the flex 108-1 within the bevel 106 enables the sensor 108 and piercing member 102 to be delivered through the skin into a subdermal space. The flex 108-1 keeps the sensor 108 in place and in close proximity to the exterior piercing tip 106-1*a* and interior piercing tip 106-2*a*. The flex 108-1 further creates a transition between exterior piercing tip 106-1*a* and sensor straight 108-3 that enables the sensor 108 and the piercing member 102 to traverse the skin via one insertion action. In some embodiments, the exterior trailing bevel 106-1*b* and the interior trailing bevel 106-2*b* are blunted or even removed and replaced by a notch. Blunting or replacing the trailing bevel with a notch reduces potential damage to the sensor during the insertion process, when the insertion force transmitted via the piercing member 102 is applied to the flex 108-1.

When the combined piercing member 102 and sensor 108 are inserted, the interior trailing bevel 106-2*b* catches the flex 108-1 thereby cooperatively inserting the sensor 108 when both the sensor 108 and the piercing member 102 is introduced into the tissue. Insertion of the piercing member 102 can be accomplished via manual manipulation of an insertion tool. Alternatively, other embodiments can rely on stored energy such as a spring or the like to supplement biomotive insertion forces. Regardless of how insertion is performed, the sensor is typically designed to be inserted a minimum depth beneath the skin. In preferred embodiments, the piercing member 102 reaches a desired depth and is subsequently retracted. Upon retraction the interior trailing bevel 106-2*b* disengages from the flex 108-1 enabling the sensor to remain at the desired insertion depth after the piercing member is withdrawn.

Figure 4A:
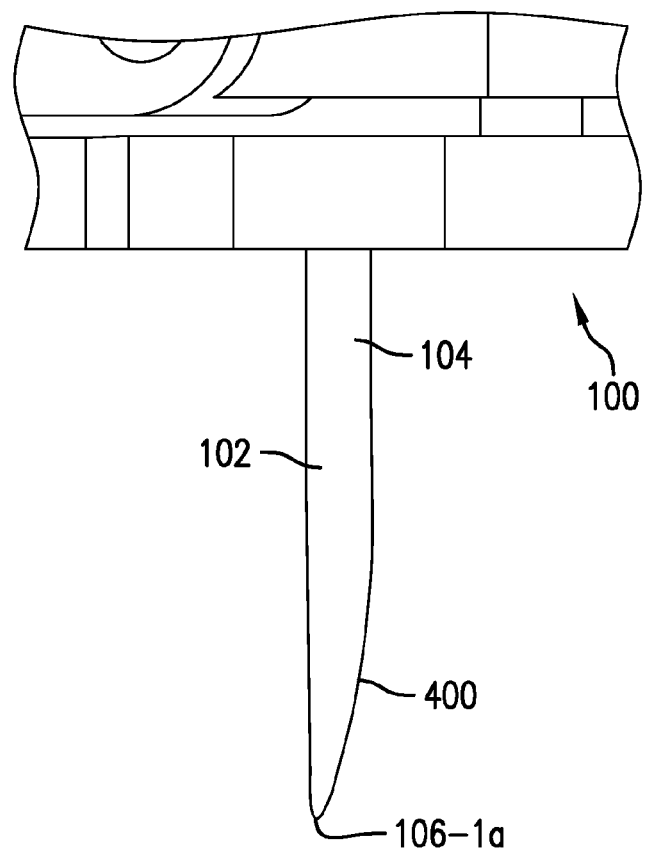
FIGS. 4A and 4B are exemplary pseudo-isometric views of the sensor assembly, specifically
Figure 4B:
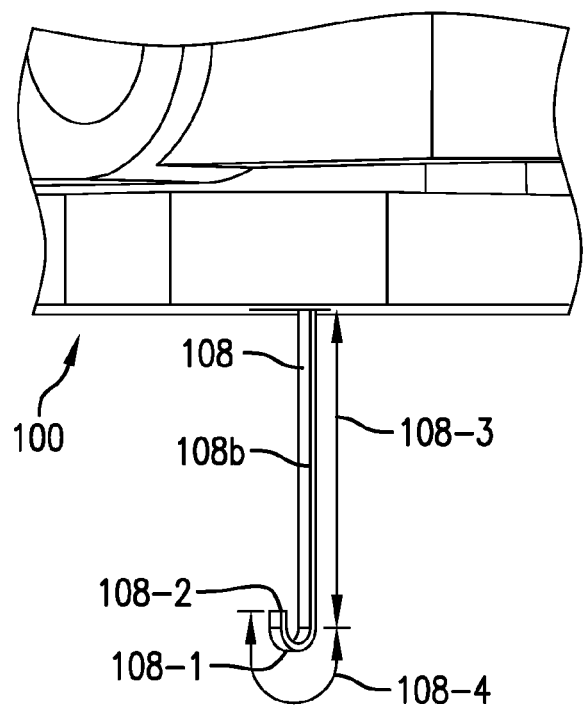

FIGS. 4A and 4B are exemplary pseudo-isometric views of the sensor assembly 100, specifically FIG. 4A illustrates the piercing member 102 while FIG. 4B illustrates the sensor 108 without the piercing member, in accordance with embodiments of the present invention. FIG. 4A primarily illustrates the exterior 104 of the piercing member 102. A bevel edge 400 is clearly illustrated along with exterior piercing tip 106-1*a*. The exemplary illustration of the sensor 108 in FIG. 4B includes a clear view of b-side 108*b*. In many configurations, the b-side 108*b* is placed against the piercing member 102. In some embodiments the sensor 108, be it a single or multi-analyte sensor, has electrode components such as, but not limited to, at least one working electrode and a combined counter-reference electrode, or pseudo-reference electrode. In still other embodiments the electrode components include a more traditional three electrode structure that includes a working electrode, a counter electrode and a reference electrode. Irrespective of the number of electrode components, in some embodiments the electrode components are formed on the a-side 108*a*. In other embodiments the electrode components are formed on the b-side 108*b*. In still other embodiments, electrode components are distributed to both the a-side 108*a* and the b-side 108*b*.

In addition to electrode components being formed on either a-side 108*a* or b-side 108*b* or both a-side 108*a* and b-side 108*b*, electrode components can also be formed traversing the flex 108-1 within the distal end 108-4 and along the sensor straight 108-3. Forming electrode components on and across the flex 108-1 within the distal end 108-4 results in an effective increase in sensor area but does not require the sensor to be positioned deeper into the tissue of a subject. This can be very beneficial for multi-analyte sensors where the different working electrodes associated with each analyte require a minimum area to generate sufficient signal for the desired sensor use period. Additionally, the decreased or shallow insertion depth enabled by the increased area from the flex 108-1 can improve comfort during the insertion process.

Figure 5A:
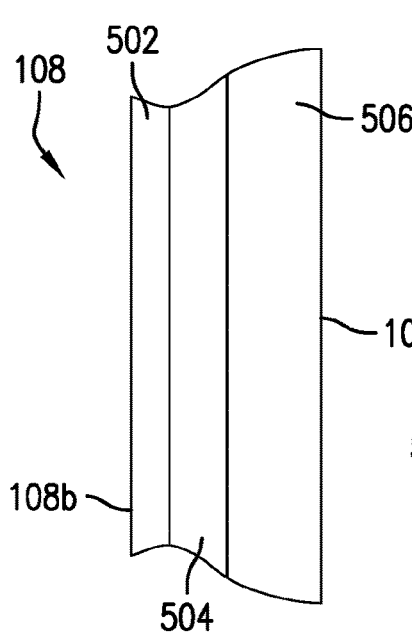
FIG. 5A is an exemplary side view of a portion of the sensor, in accordance with embodiments of the present invention.

FIG. 5A is an exemplary side view of a portion of the sensor 108, in accordance with embodiments of the present invention. Viewing the sensor 108 from the side reveals the sensor 108 is comprised of a plurality of layers. In many embodiments a first layer 502 is an insulator, a second layer 504 is an electrical conductor and a third layer 506 is actually it's own multi-layered structure of a plurality of layers patterned over the second layer 504 to achieve the desired sensing properties. In most embodiments an adhesive layer bonds the first layer 502 to the second layer 504. Similarly, the third layer 506 often includes an insulative layer adjacent to the second layer 504 that is patterned to expose select portions of the second layer 504. Additionally, the second layer 504 is typically patterned to create various electrode components such as, but not limited to working electrodes, counter electrodes, reference electrodes and pseudo-reference electrodes.

In preferred embodiments the second layer 504 is often selected to be a stainless steel material. In many embodiments, the second layer 504 undergoes additional processing such as electroplating to further enhance properties such as, but not limited to electrical conductivity. Accordingly, in many embodiments, the selection of the electrical conductor can encompass multiple requirements such as electrical conductivity, ease of plating as well as mechanical properties that enable the flex 108-1 such as thickness, ductility and toughness.

Figure 5B:
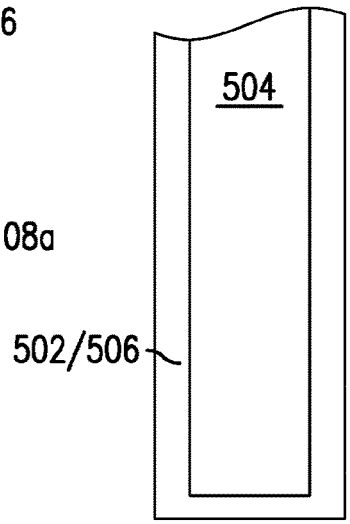
FIG. 5B is an exemplary top view of a portion of the sensor, in accordance with embodiments of the present invention.

FIG. 5B is an exemplary top view of a portion of the sensor 108, in accordance with embodiments of the present invention. In FIG. 5B the distal end 108-4 along with the terminal end 108-2 of the sensor is illustrated. Exemplary working electrodes 510 are included on layer 504 to illustrate that electrode components can be placed where the flex is to be formed. In other embodiments, different electrode components such as, but not limited to pseudo-reference electrodes, counter electrodes and reference electrodes can be formed within the distal end 108-4. For illustrative purposes, first layer 502 and third layer 506 are illustrated extending beyond the second layer 504. In many embodiments, the various layers of the sensor 108 are cut flush along the edges resulting in edges of the first layer 502, second layer 504 and third layer 506 being exposed along the edges of the sensor 108.

Figure 5C:
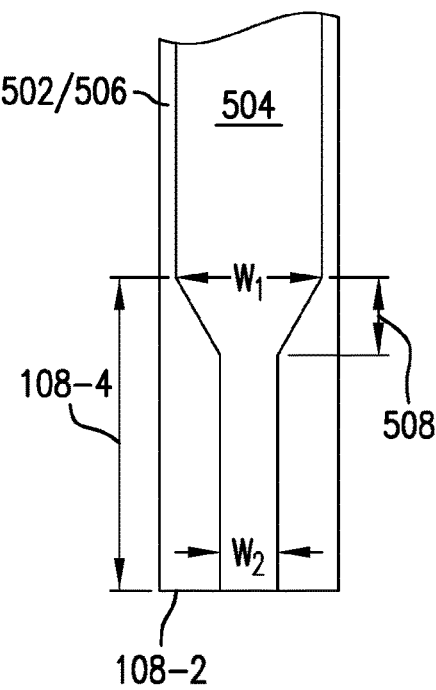
FIGS. 5C and 5D are top views of exemplary configurations of sensors where the physical properties of the flex are modified by changing some aspect of at least one layer of the sensor, in accordance with embodiments of the present invention.
Figure 5D:
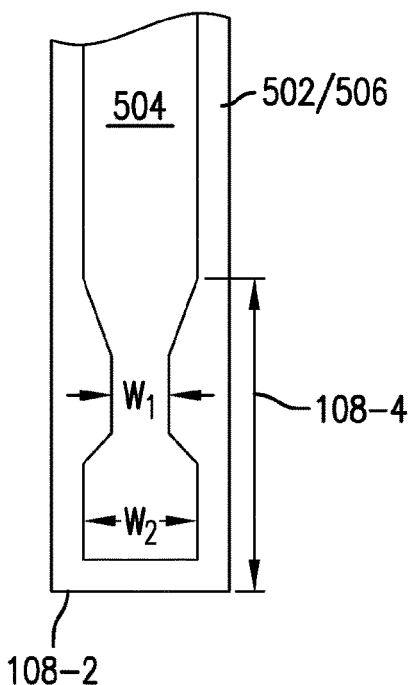

FIGS. 5C and 5D are top views of exemplary configurations of sensors where the physical properties of the flex 108-1 are modified by changing some aspect of at least one layer of the sensor 108, in accordance with embodiments of the present invention. In most embodiments the layer most likely to be modified is the second layer 504 because it is an electrical conductor. An exemplary modification to the second layer 504 includes, but is not limited to patterning the second layer 504 within the flex. In FIG. 5C the second layer 504 approaches the distal end 108-4 at a first width W1 but within the distal end 108-4, the width is modified to a second width W2. It may be beneficial to remove material from the flex in order to achieve desired mechanical properties. The removal of the second layer 504 within the distal end 108-4 can be accomplished during the patterning process where electrical traces and electrode structure are initially defined. Alternatively, the distal end 108-4 can be shaped during a singulation process resulting in the second width W2 being less than the first width W1. Singulation of the sensor from a large sheet can be accomplished using techniques such as, but not limited to laser cutter, die cutting, water jet cutting and the like.

FIG. 5D is an exemplary sensor 108 where the flex within the distal end 108-4 is a second width W2 and the remained of the sensor has a first width W1. Similar to the embodiment shown in FIG. 5C, the modifications in FIG. 5D can be made while initially patterning the second layer 504 or during a singulation process. Other modifications to a layer within the sensor 108 include reducing the thickness of the second layer 504. In FIGS. 5C and 5D, with width of the second layer was modified. However, the thickness (e.g. the thickness of the second layer 504 when viewed from the side) can be modified to be thinner or thicker. Thinning the second layer 504 can be accomplished by physically removing the material via a mechanical, electro chemical or electro-mechanical operations. Alternatively, thickening a layer may be accomplished via the addition of materials either by selective placement via adhesive bonding or similar operation. It may be desirable to thin the conductive layer to achieve a more flexible flex. On the other hand, it may be desirable to thicken or reinforce the conductive layer to improve toughness or to ensure the flex does not break.

Figure 5E:
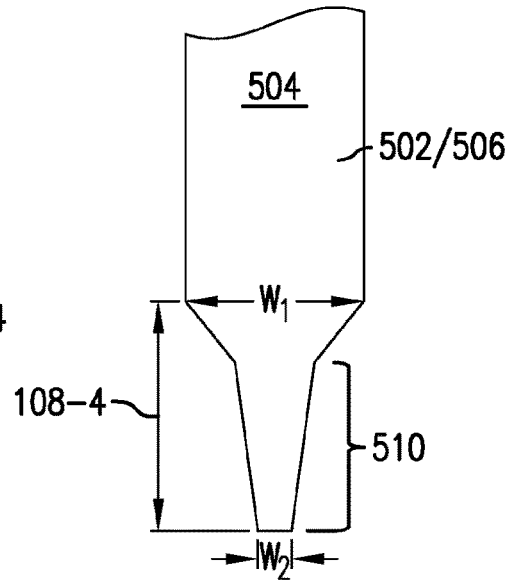
FIG. 5E is another exemplary distal end of the sensor configured to minimize or reduce the terminal end width, in accordance with embodiments of the present invention.

FIG. 5E is another exemplary distal end 108-4 of the sensor 108 configured to minimize or reduce the terminal end 108-2 width W2, in accordance with embodiments of the present invention. In FIG. 5E the terminal end 108-2 width W2 is significantly reduced from the sensor width W1. In many embodiments, the distal end 108-4 includes a single or multiple tapers (e.g. 510a and 510b) that reduce with width of the sensor from W1 to W2. The rationale for changing the sensor width to W2 is to enable the terminal end 108-2 to fit within the bevel of the piercing member. In embodiments where the sensor width does not taper, it may require the use of a relatively large piercing member to accommodate the full width of the sensor. However, by tapering the terminal end to a reduced, more desired width, the insertion force necessary to pierce the skin can be reduced along with decreasing the width of the piercing member. In some embodiments the piercing member is a needle of a common gauge. In some embodiments the needle is selected from a range of gauges between 20 and 30.

While most of the discussion has been focused on modifying the second layer 504 other layers within the sensor can be modified to augment or enhance mechanical properties of the flex. Recall that third layer 506 (FIG. 5A) is actually it's own multilayer structure. Accordingly, mechanical properties of the flex can be tuned via modification of a layer or layers within the third layer 506. In many embodiments, the sensors will be formed on using the manufacturing processes described in U.S. patent application Ser. No. 15/472,194 filed on Mar. 28, 2017 and PCT/US18/38984 filed on Jun. 22, 2018 and Ser. No. 16/152,727 filed on Oct. 5, 2018, each of which are herein incorporated by reference for all purposes. In many embodiments, after the sensors are formed and singulated, the flex will be introduced or formed as part of installing or placing the sensor within the sensor assembly or insertion tool that will eventually be used to insert the sensor.

In many embodiments the flex 108-1 accomplishes a plurality of goals. One goal is to implant a sensor with enough surface area for multi-analyte sensing at a minimal depth or shallow depth. Having the sensor element formed across the flex results in a larger sensor surface area at an insertion depth that is less than a comparable straight sensor. Another goal is to reliably implant the sensor to the desired depth. The flex helps accomplish this goal because during insertion it temporarily couples the sensor to the trailing edge of the piercing member. Furthermore, upon withdrawal of the piercing member, the flex decouples from the trailing edge of the piercing member allows the piercing member to be cleanly removed. Additional benefits of the flex includes improved mechanical stability throughout the sensor wear period as the flex can provide resistance thereby reducing the likelihood of accidentally pulling out the sensor.

Figures 6A, 6B, 6C, 6D:
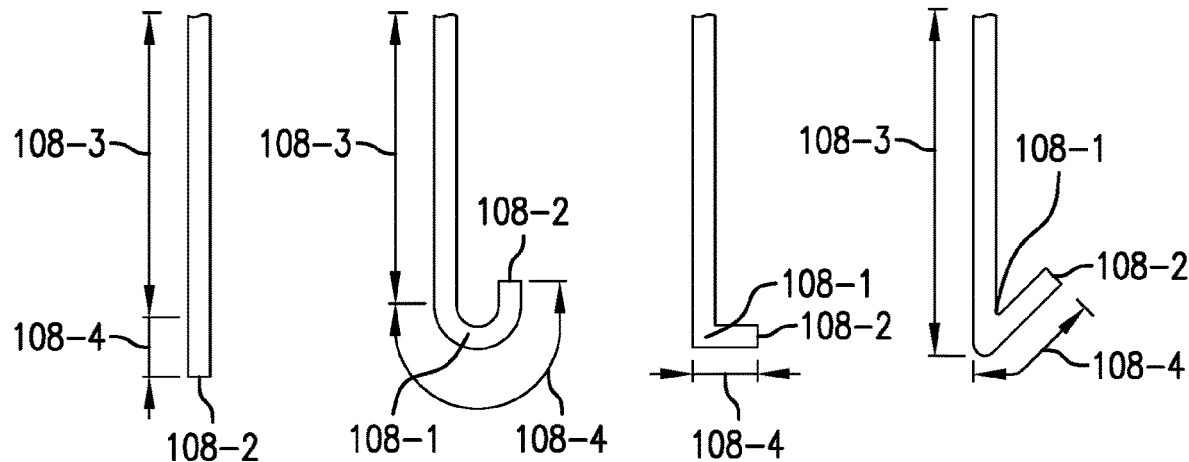
FIG. 6A is an exemplary illustration of a side view of a singulated sensor before the flex is formed on the distal end, in accordance with embodiments of the present invention.
FIGS. 6B-6D are exemplary illustration of a side view of a singulated sensor after the flex is formed on the distal end, in accordance with embodiments of the present invention.

FIG. 6A is an exemplary illustration of a side view of a singulated sensor before the flex is formed on the distal end, in accordance with embodiments of the present invention. The sensor is essentially straight and flat. FIGS. 6B-6D are exemplary illustration of a side view of a singulated sensor after the flex is formed on the distal end, in accordance with embodiments of the present invention. The basic u-shaped flex is what was used in most of the illustrations accompanying this document. However, the flex can take other shapes such as those found in FIGS. 6C and 6D.

FIG. 6C is an exemplary illustration where the distal end of the sensor 108 is substantially perpendicular to the sensor straight 108-3. In this embodiment the terminal end 108-2 would be placed within the interior of the piercing member. During insertion, the trailing bevel would interact with the flex 108-1 and require the flex 108-1 to endure the insertion force without straightening out the flex or enabling the piercing member to slip past the flex. FIG. 6D is an alternative embodiment where an acute angle is formed between the flex 108-1 and the sensor straight 108-3. These embodiments may reduce the likelihood of the piercing member slipping past the flex but may also require a more robust flex to ensure the electrical conductor does not break due to the bending of the flex. In each of the embodiments illustrated in FIGS. 6B-6D, the flex is intended to resist the shear force imparted by the piercing member on the flex during insertion. However, when the sensor is removed, preferred embodiments of the flex do not rigidly maintain the flex. In other words, the flex does not retain the flex shape when it is removed after being worn for its duration period. Specifically, the mechanical properties of the flex are tuned to enable the flex to substantially deform to allow the entire sensor to be removed without breaking. In many embodiments, in addition to tuning mechanical properties, physical properties such as, but not limited to the length and width of the conductor 504 and the sensor 108 can be selected or optimized to keep the terminal end retained within the needle during insertion yet easily deformable from the flexed position to a relaxed position during removal.

Figures 7A, 7B:
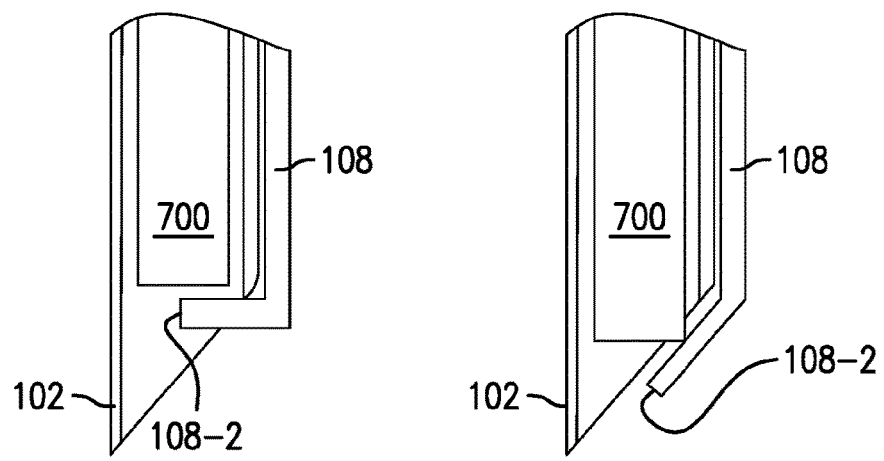
FIGS. 7A and 7B are exemplary illustrations of a sensor having a flex that further uses an ejector during the insertion process to ensure the sensor is properly deployed from the piercing member, in accordance with embodiments of the present invention.

FIGS. 7A and 7B are exemplary illustrations of a sensor 108 having a flex that further uses an ejector 700 during the insertion process to ensure the sensor is properly deployed from the piercing member, in accordance with embodiments of the present invention. In FIG. 7A the sensor 108 has been inserted to the desired depth. In some embodiments an ejector 700 is employed to forcibly eject the terminal end 108-2 from the piercing member 102. As illustrated, the ejector 700 can be an implement that is contained within the piercing member that physically contacts the terminal end 108-2 and dislodges it from the piercing member. During insertion of the piercing member and the sensor, the ejector 700, piercing member 102 and sensor 108 move together into the subject. After reaching the desired insertion depth, in one embodiment the piercing member is retracted while the ejector 700 remains stationary. If the sensor attempts to be withdrawn with the piercing member, the terminal end of the sensor contacts the ejector 700 allowing the piercing member to withdrawn. Eventually, the piercing member is withdrawn, preferably at a rate where it is hidden within the piercing member.

In another embodiment, as illustrated in FIG. 7B, after reaching the desired insertion depth, the ejector 700 continues to be inserted resulting in the ejector contacting and displacing the terminal end 108-2 from the interior of the piercing member 102. After displacing the sensor, the ejector and the piercing member can be withdrawn from the subject. The two embodiments discussed regarding the operation of the ejector are exemplary and should not be construed as limiting. Further embodiments can utilize an ejector that manages to displace the terminal end 108-2 from the interior of the piercing member in any number of different ways.

Figure 8A:
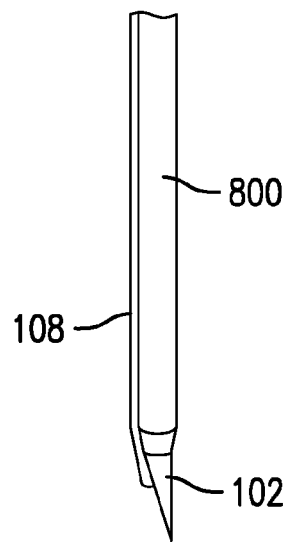
FIGS. 8A-8D are exemplary illustrations how a sensor with a flex can be integrated into a combined sensor and infusion device, in accordance with embodiments of the present invention.

The mechanical properties of the sensor, particularly the distal end and the flex are extremely important in enabling proper insertion and eventual withdrawal of the sensor. It would be highly disadvantageous if distal ends of sensors were breaking off and remaining in subjects. Accordingly, selection of materials and forming of materials is critically important. It is further desired to FIGS. 8A-8D are exemplary illustrations how a sensor with a flex can be integrated into a combined sensor and infusion device, in accordance with embodiments of the present invention. FIG. 8A is an exemplary illustration of a sensor 108 with a distal end within a piercing member 102 during the insertion process. How FIG. 8A differs from FIG. XX is the inclusion of optional cannula 800. In some embodiments, the inclusion of optional cannula 800 transforms what was simply the implantation of the sensor into subdermal space to the implantation of a combined sensor and infusion device. Operation as a combined infusion set and sensor can simplify the use of a closed-loop artificial pancreas system. With a separate sensor and infusion set, the user must endure multiple insertion at potentially different time intervals. With a combined sensor and infusion set, the user of an artificial pancreas only needs to perform a single insertion and only keep track of rotating a single insertion site.

Figure 8B:
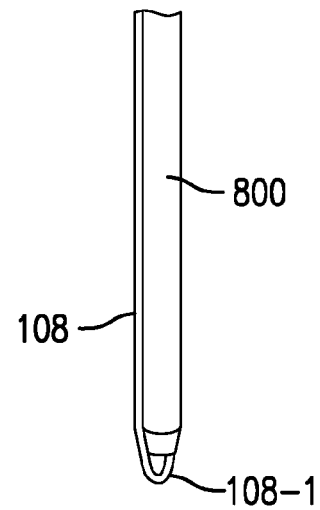

FIG. 8B is an exemplary pseudo-isometric view of a combined sensor and infusion set after the piercing member has been retracted, thereby leaving the sensor 102 and the cannula 800 behind. With the piercing member having been withdrawn or retracted, the terminal end 108-2 of the sensor 108 may remain within the cannula 800. Recall that in some embodiments the distal end that encompasses the flex 108-1 can include electrode structure. Because some electrode structure may be found on the distal end it may be desirable to remove the distal end from the interior or the cannula to avoid or minimize interference from an infusate.

Figure 8C:
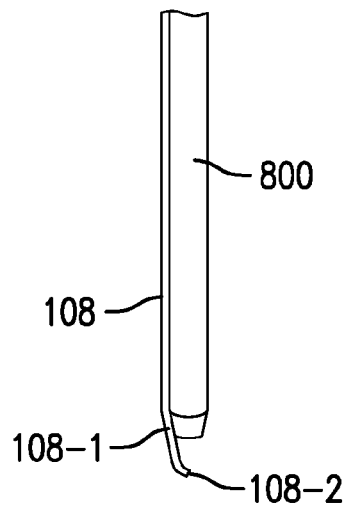

FIG. 8C is an exemplary pseudo-isometric view of a combined sensor and infusion set after the piercing member has been retracted and an optional ejector (not shown) has ejected the terminal end 108-2 of the sensor 108 from the cannula 800, in accordance with embodiments of the present invention. As discussed above regarding FIGS. 7A and 7B, an ejector can assist in the ejection of the terminal end 108-2 from the cannula 800. As discussed above, in some embodiments the ejector is a separately moving part within the piercing member that pushes, or ejects, the terminal end 108-2 after the piercing member has placed the sensor and cannula at the desired insertion depth. In other embodiments, the ejector can remain stationary within the piercing member and the sensor and/or cannula can be retracted thereby driving the terminal end 108-2 into the stationary ejector, and displacing the terminal end from the cannula 800. After being ejected from the cannula, the terminal end 108-2 can retain some evidence of the flex 108-1. After displacing the terminal end 108-2 from the cannula 800, there is a possibility of infusate interfering with the operation of the sensor 108. Accordingly, in some embodiments, it may be desirable to improve diffusion of the infusate into the surrounding tissue.

Figure 8D:
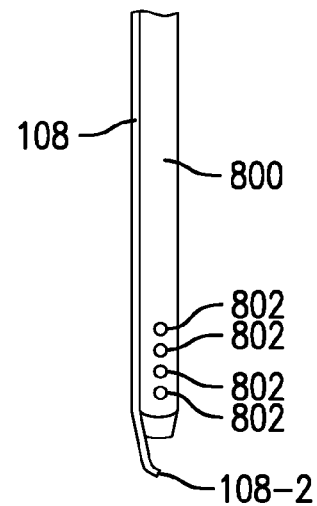

FIG. 8D is an exemplary pseudo-isometric view of a combined sensor and infusion where the cannula 800 includes perforations 802 to enable diffusion of the infusate into surrounding tissue, in accordance with embodiments of the present invention. The number and location of perforations 802 should be considered exemplary rather than limiting. Various embodiments include different numbers of perforations at various locations around the cannula. Because the sensor straight can include electrode components, it may be undesirable to include perforations immediately adjacent to, or within close proximity of the sensor 108. However, perforations on the cannula on a side opposite the sensor 108 would seem preferable from a distance and potential interference standpoint.

The embodiments discussed above are intended to be exemplary. For example, while many of the embodiments are related to continuous glucose sensing, other embodiments can be related to generic subdermal sensing for analytes or compounds such as, but not limited to lactate, ketones, oxygen and the like. In many embodiments, additional features or elements can be included or added to the exemplary features described above. Alternatively, in other embodiments, fewer features or elements can be included or added to the exemplary features described above. In still other embodiments, where possible, combination of elements or features discussed incongruously may be combined together in a single embodiment rather than in discretely in the exemplary discussion. The flex of a sensor can be configured based on mechanical properties, physical properties, or combination thereof.

Accordingly, while the description above refers to particular embodiments of the invention, it will be understood that many modifications may be made without departing from the spirit thereof. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

The invention claimed is:

1. A sensor assembly, comprising:
   a piercing member having an interior and exterior, and
   a sensor having a proximal end and a distal end separated by a sensor straight, the distal end including a flex being terminated at a terminal end, the terminal end being within the interior of the piercing member, the sensor straight being adjacent to the exterior of the piercing member, the flex including a first layer, a second layer, and a third layer,
   wherein the first layer is composed of an insulator,
   wherein the second layer is disposed between the first and third layers,
   wherein the second layer is composed of an electrical conductor,
   wherein the second layer has a first width, a second width, and a third width,
   wherein the first width has a first width value,
   wherein the third width has the first width value,
   wherein the second width is located intermediate of the first and third widths, wherein the second width has a second width value less than the first width value.

2. The sensor assembly of claim 1, wherein the sensor includes an a-side and a b-side, the b-side being in contact with the exterior of the piercing member.

3. The sensor assembly of claim 1, wherein the piercing member includes a bevel having an exterior piercing tip, an interior piercing tip, an interior trailing bevel and an exterior trailing bevel.

4. The sensor assembly of claim 1, wherein the flex includes an electrode structure.

5. The sensor assembly of claim 1, further including a cannula having a cannula interior and a cannula exterior, the piercing member being within the cannula interior.

6. The sensor assembly of claim 1, further including an ejector, the ejector being within the interior of the piercing member, the ejector displacing the terminal end of the sensor from the interior of the piercing member after the sensor is inserted to a desired insertion depth.

7. The sensor assembly of claim 6, further including an ejector, the ejector being within the interior of the piercing member, the ejector displacing the terminal end of the sensor from the interior of the piercing member after the sensor is inserted to a desired insertion depth.

8. The sensor assembly of claim 1, wherein the terminal end has a terminal width being sized to fit within the piercing member.

9. The sensor assembly of claim 1, wherein the flex is bent.

10. The sensor assembly of claim 1, wherein the second layer is composed of a stainless steel material.

11. The sensor assembly of claim 1, wherein the second layer is electroplated.

12. A method of inserting a sensor into a subdermal space, the method comprising the operations of:
coupling a sensor to a piercing member, the sensor having a distal end, the distal end including a flex that terminates in a terminal end, the flex enabling placement of the terminal end of the sensor within a piercing bevel of the piercing member, the flex including a first layer, a second layer, and a third layer,
wherein the first layer is composed of an insulator,
wherein the second layer is disposed between the first and third layers,
wherein the second layer is composed of an electrical conductor,
wherein the second layer has a first width, a second width, and a third width,
wherein the first width has a first width value,
wherein the third width has the first width value,
wherein the second width is located intermediate of the first and third widths,
wherein the second width has a second width value less than the first width value;
inserting the piercing member to a depth within the subdermal space, the sensor coupled to the piercing member being inserted to the same depth as the piercing member; and
retracting the piercing member, the retraction of the piercing member decoupling the terminal end from within piercing bevel of the piercing member.

13. The method of claim 12, further including the operation of ejecting the terminal end from within the piercing bevel of the piercing member.

14. The method of claim 12, wherein the flex is bent.

15. The method of claim 12, wherein the second layer is composed of a stainless steel material.

16. The method of claim 12, wherein the second layer is electroplated.

17. A sensor, comprising:
a sensor body;
a proximal end; and
a distal end separated from the proximal end by the sensor body, the distal end including a flex being terminated at a terminal end, the flex including a first layer, a second layer, and a third layer,
wherein the first layer is composed of an insulator,
wherein the second layer is disposed between the first and third layers,
wherein the second layer is composed of an electrical conductor,
wherein the second layer has a first width, a second width, and a third width,
wherein the first width has a first width value,
wherein the third width has the first width value,
wherein the second width is located intermediate of the first and third widths,
wherein the second width has a second width value less than the first width value.

18. The sensor of claim 17, wherein the flex is bent.

19. The sensor of claim 17, wherein the second layer is composed of a stainless steel material.

20. The sensor of claim 17, wherein the second layer is electroplated.

* * * * *